United States Patent
Meijers et al.

(10) Patent No.: US 12,070,622 B2
(45) Date of Patent: Aug. 27, 2024

(54) SYSTEM AND METHOD FOR RADIOTHERAPY FIELD DELIVERY TIME OPTIMIZATION

(71) Applicant: Varian Medical Systems, Inc., Palo Alto, CA (US)

(72) Inventors: Arturs Meijers, Palo Alto, CA (US); Perttu Niemela, Espoo (FI); Roni Hytonen, Palo Alto, CA (US); Reynald Van der Straeten, Brussels (BE); Jan Timmer, Los Altos, CA (US); Timo Koponen, Espoo (FI); Christel Smith, Santa Barbara, CA (US); Isabel Huth, Kuerten (DE)

(73) Assignees: VARIAN MEDICAL SYSTEMS THERAPY GMBH & CO KG, Troisdorf (DE); VARIAN MEDICAL SYSTEMS INTERNATIONAL AG, Cham (CH); VARIAN MEDICAL SYSTEMS, Palo Alto, CA (US)

( * ) Notice: Subject to any disclaimer, the term of this patent is extended or adjusted under 35 U.S.C. 154(b) by 912 days.

(21) Appl. No.: 17/137,222

(22) Filed: Dec. 29, 2020

(65) Prior Publication Data
US 2022/0176156 A1 Jun. 9, 2022

Related U.S. Application Data

(63) Continuation-in-part of application No. 17/115,639, filed on Dec. 8, 2020, now abandoned.

(51) Int. Cl.
*A61N 5/10* (2006.01)

(52) U.S. Cl.
CPC ......... *A61N 5/1031* (2013.01); *A61N 5/1043* (2013.01)

(58) Field of Classification Search
None
See application file for complete search history.

(56) References Cited

U.S. PATENT DOCUMENTS

| | | | |
|---|---|---|---|
| 2015/0080631 A1* | 3/2015 | Pu | A61N 5/1043 600/1 |
| 2020/0129781 A1* | 4/2020 | Engwall | A61N 5/1043 |
| 2021/0213303 A1* | 7/2021 | Bokrantz | A61N 5/1045 |

FOREIGN PATENT DOCUMENTS

| | | |
|---|---|---|
| EP | 3421085 | 1/2019 |
| WO | 2020/177844 | 9/2020 |

OTHER PUBLICATIONS

Schell Stefan et al.: "Advanced Treatment Planning Methods for Efficient Radiation Therapy with Laser Accelerated Proton and Ion Beams," Medical Physics, AIP, Melville, NY, US, vol. 37, No. 10, Sep. 20, 2010, pp. 5330-5340, XP012144701, ISSN: 0094-2405, DOI: 10.1118/1.3491406.

* cited by examiner

*Primary Examiner* — Thaddeus B Cox
(74) *Attorney, Agent, or Firm* — Harness, Dickey & Pierce, P.L.C.

(57) ABSTRACT

Treatment fields can be produced as part of a treatment plan that achieves a desired balance between field delivery time and dose based on machine parameters and knowledge, such as machine-specific beam production, transport and scanning logic, and/or a maximum treatment time value. The treatment parameters can be adjusted using a graphical user interface so that treatment time or dosimetry is prioritized. As a result, the overall treatment time is reduced, and hence treatment quality and patient experience are improved.

20 Claims, 14 Drawing Sheets

Plan 3: Plan With Shorter Delivery Time

Plan 4: Plan With Longer Delivery Time 1100 (1110)

SYSTEM AND METHOD FOR RADIOTHERAPY FIELD DELIVERY TIME OPTIMIZATION

RELATED U.S. APPLICATION

This application is a continuation-in-part of the application with Ser. No. 17/115,639, entitled "System and Method for Radiotherapy Field Delivery Time Optimization," by A. Meijers et al., filed Dec. 8, 2020, and hereby incorporated by reference in its entirety.

FIELD

Embodiments of the present invention generally relate to the field of radiotherapy. More specifically, embodiments of the present invention relate to computer-implemented treatment planning methods and systems for radiotherapy treatment.

BACKGROUND

One goal of radiotherapy treatment and biological planning is to maximize the dose supplied to a target tumor while minimizing the dose absorbed by the surrounding (normal) tissue. Treatment outcomes regarding tumor control and normal tissue toxicities not only depend on physical parameters, such as dose, but also depend on a multitude of other parameters such as biological parameters and machine parameters.

While maximizing the dose supplied to a target tumor while minimizing the dose absorbed by the surrounding tissue remains a primary consideration, other factors may be considered to improve the quality of treatment and/or the experience of the patient receiving the treatment. For example, in many cases it may be desirable to reduce or limit the overall treatment time and/or a time of an individual treatment fraction. In some situations, the treatment can be applied while the patient is holding their breath to remain still. However, in existing approaches to treatment planning that attempt to minimize the dose absorbed by surrounding healthy tissue, it is difficult to accommodate certain types of radiotherapy treatment that are based on relatively short treatment times.

One radiation therapy technique is known as spot scanning, also known as pencil beam scanning. In spot scanning, a beam is directed to spots in a treatment target prescribed by the treatment plan. The prescribed spot positions are typically arranged in a fixed (raster) pattern for each energy layer of the beam, and the beam is delivered on a fixed scanning path within an energy layer. While some existing treatment planning solutions may remove spots below a certain monitor unit (MU) threshold after optimization, the resultant dose is redistributed in a way that is not necessarily optimal in terms of plan quality or field delivery time, from the perspective of treatment delivery equipment.

SUMMARY

Accordingly, a need exists in the art to generate treatment plans for radiotherapy using treatment time as a parameter (optimization objective), for example, to reduce the overall treatment time or to limit the overall treatment time to an acceptable value while still maintaining clinically acceptable dosimetry. Embodiments of the present invention are operable to produce treatment fields as part of a treatment plan that achieves a desired balance between field delivery time and dose based on machine parameters and knowledge, such as machine-specific beam production, transport and/or scanning logic, and/or a maximum treatment time value, and in which the treatment parameters can be adjusted so that treatment time or dosimetry is prioritized using a graphical user interface.

Embodiments of a computer-implemented method for radiotherapy treatment planning are disclosed. In embodiments, the method includes: accessing a radiotherapy treatment plan including one or more treatment (energy) layers, where each of the treatment layers includes a number of spots; receiving a weight for a treatment time objective of the radiotherapy treatment plan, modifying a spot from a treatment layer based on the weight and a cost of the spot to produce a modified layer, or reducing the number of layers; and generating a modified radiotherapy treatment plan using the modified layer or the reduced number of layers, where the modified radiotherapy treatment plan is operable to be executed by a delivery machine to apply radiotherapy treatment to a target in accordance with the modified radiotherapy treatment plan.

According to some embodiments, the method also includes modifying one or more of the spots to produce one or more modified layers, where the modified radiotherapy treatment plan is generated using the modified layers.

According to some embodiments, the spot is modified to redistribute a dose contribution of the spot to one or more neighboring spots.

According to some embodiments, a weight for a dosimetric objective of the radiotherapy treatment plan is also received.

According to some embodiments, the dosimetric objective includes at least one of: a dose-volume histogram (DVH) objective; an equivalent uniform dose (EUD) objective; a minimum dose objective; a maximum dose objective; and a dose fall-off objective.

According to some embodiments, the method includes dynamically rendering a dose-volume histogram on a graphical user interface of a treatment planning system based on the weight for the treatment time objective of the modified radiotherapy treatment plan and the weight for the dosimetric objective of the radiotherapy treatment plan.

According to some embodiments, the weight for the treatment time objective of the modified radiotherapy treatment plan and the weight for the dosimetric objective are defined according to user input received from a controller (such as a slider) rendered on the graphical user interface of the treatment planning system.

According to some embodiments, the method includes simulating a radiotherapy treatment according to the modified radiotherapy treatment plan to determine if an actual dose, when applied according to the modified radiotherapy treatment plan, will conform with a predefined quality standard for treatment.

According to some embodiments, modifying a spot from a treatment layer includes calculating a cost for each of the spots based on a dose associated with the spot and a delivery duration of the spot, and modifying at least one of the spots having the highest cost.

According to another embodiment, an electronic system for radiotherapy treatment planning is disclosed. The electronic system includes a display device, a memory, and a processor in communication with the memory. The processor is operable to execute instructions for performing a method of radiotherapy treatment planning. The method includes: accessing a radiotherapy treatment plan including one or more treatment layers, where each of the treatment layers includes a number of spots; receiving a weight for a treatment time objective of the radiotherapy treatment plan, modifying a spot from a treatment layer based on the weight and a cost of the spot to produce a modified layer, or reducing the number of layers; and generating a modified radiotherapy treatment plan using the modified layer or reduced number of layers, where the modified radiotherapy treatment plan is operable to be executed by a delivery machine to apply radiotherapy treatment to a target in accordance with the modified radiotherapy treatment plan.

According to a different embodiment, a non-transitory computer-readable storage medium embodying instructions that are executed by a processor to cause the processor to perform a method of radiotherapy treatment planning is disclosed. The method includes: accessing a radiotherapy treatment plan including one or more treatment layers, where each of the treatment layers includes a number of spots; receiving a weight for a treatment time objective of the radiotherapy treatment plan, modifying a spot from a treatment layer based on the weight and a cost of the spot to produce a modified layer, or reducing the number of layers; and generating a modified radiotherapy treatment plan using the modified layer or reduced number of layers, where the modified radiotherapy treatment plan is operable to be executed by a delivery machine to apply radiotherapy treatment to a target in accordance with the modified radiotherapy treatment plan.

The reduction of treatment time is significant for improving the quality of the treatment as well as patient comfort. Reducing treatment time for delivering a radiotherapy treatment plan can lower the risk of intra-fraction misalignment, increase machine throughput, and enable or facilitate specialized treatments, such as breath-hold immobilization treatments, thereby improving the quality of care and/or accessibility to the proton therapy.

These and other objects and advantages of embodiments according to the present invention will be recognized by one skilled in the art after having read the following detailed description, which are illustrated in the various drawing figures.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
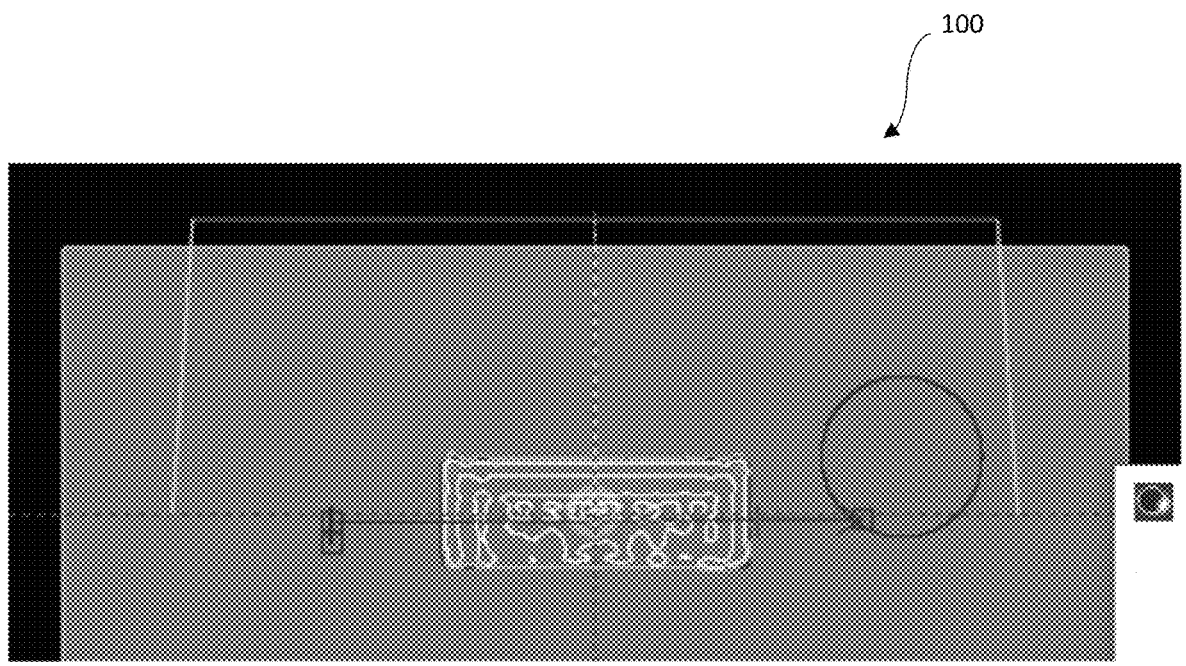
FIG. 1 is a diagram of the isodose lines of an example of a radiotherapy treatment plan generated by a treatment planning system according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Some embodiments may be described in the general context of computer-executable instructions, such as program modules, executed by one or more electronic systems (computers or other devices). Generally, program modules include routines, programs, objects, components, data structures, etc. that perform particular tasks or implement particular abstract data types. Typically, the functionality of the program modules may be combined or distributed as desired in various embodiments.

Portions of the detailed description that follows are presented and discussed in terms of a method. Although steps and sequencing thereof are disclosed in a figure herein (e.g., FIG. 12) describing the operations of this method, such steps and sequencing are only examples. Embodiments are well-suited to performing various other steps or variations of the steps recited in the flowchart of the figure herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "displaying," "writing," "including," "storing," "transmitting," "traversing," "determining," "identifying," "observing," "adjusting," "receiving," "modifying," "generating," "redistributing," "simulating," or the like, refer to the action and processes of an electronic (e.g., computer) system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Systems and Methods for Radiotherapy Field Delivery Time Optimization

According to embodiments of the present invention, beam currents of a proton or ion beam, or the number of protons or ions per time segment, may be adjusted to minimize the time required to treat a target volume with radiation. The beam currents of the proton or ion beam, or the number of protons or ions per time segment, may be adjusted according to a treatment plan and also according to one or more limitations to the treatment machine equipment that produces the proton or ion beam and delivers and monitors the radiation dose. The treatment plan may be based on one or more computerized tomography (CT) images, and/or other suitable images derived from a suitable imaging technique, of the target volume of the patient's body (e.g., a cancerous tumor), and may include one or more prescriptions for an amount of radiation to deliver to the target volume, as well as multiple locations within the target volume to deliver the radiation.

To deliver the prescribed dose of radiation, the treatment plan may be converted to machine parameters (e.g., beam currents of the proton or ion beam, the number of protons or ions per time segment to be emitted by the accelerator, magnet currents, settings to achieve the prescribed energy of protons or ions at the target volume, measurement range of dose monitor system, etc.). This conversion may take into account the limitations of the treatment machine's equipment that produces the proton or ion beam and that delivers and monitors the radiation treatment.

Specialized software may be used to generate the treatment plan, and an algorithm or process may be applied that calculates the beam currents of the proton or ion beam, or the number of protons or ions per time segments, so that the patient is treated as fast as possible or to achieve a desired balance between treatment time and dosimetric objectives. In addition, the algorithm or process can determine the duration of each spot of a field, taking into account the time-optimized beam currents of the proton or ion beam, or the time-optimized number of protons or ions per time segments. The determined durations of each spot and of the whole field can be taken into account in developing the treatment plan.

FIG. 1 depicts isodose lines 100 of an example of a radiotherapy treatment plan generated by a radiotherapy treatment planning system (TPS) and used to control a radiotherapy delivery system (e.g., a proton therapy treatment system) for delivering a controlled dose of radiation, according to embodiments of the present invention. In the example of FIG. 1, a single field treatment plan including multiple energy layers is generated to deliver a 50 Grays (Gy) dose in 25 individual treatment sessions (fractions) using a fractional dose of two Gy. The treatment plan is configured to apply radiotherapy treatment using eight energy layers and 2969 total spots. Each spot is defined by an energy, a spot position for delivering a dose by the beam, and a number of monitor units (MUs) that comprise the dose. The treatment time for the different spots is determined by taking into account machine-specific parameters (e.g., timing constraints) and is summed to determine the total field irradiation time as represented in an example below in Table I.

TABLE I

| Layer Number | Energy [MEV] | Number Of Spots | Total Irradiation Time [sec] |
|---|---|---|---|
| 1 | 131.25 | 422 | 66.681 |
| 2 | 127.75 | 388 | |
| 3 | 124.25 | 367 | |
| 4 | 120.75 | 368 | |
| 5 | 117.25 | 370 | |
| 6 | 113.75 | 369 | |
| 7 | 110.25 | 293 | |
| 8 | 106.75 | 392 | |

As depicted in Table I, the example treatment plan includes a total irradiation time of 66.681 seconds. The spots of the treatment plan can be defined using machine-specific knowledge, such as a function based on machine parameters corresponding to delivery of the particular plan, field, layer or spot. For example, the parameters may include the cyclotron beam current, the number of MUs indicating the actual dose delivered for a specific plan or spot, the delivery time, the beam current in the nozzle, the magnet sweeping speed characteristics, scanning logic, and other parameters related to the specific machine or system that delivers the radiotherapy treatment.

In general, the cost of a spot of a treatment plan is a function of parameters such as, but not limited to, one or more of the following: the time required to deliver the spot, the MUs for the spot, the cyclotron beam current during the delivery of the spot, and the maximum possible cyclotron beam current, as well as other spot or beam production, transport, and delivery system parameters. In embodiments, the cost of a spot of a treatment plan may be expressed according to machine-specific knowledge using equations such as but not limited to:

$$c_{spot} = \frac{t_{spot}}{MU_{spot}} \text{ or}$$

$$c_{spot} = \frac{t_{spot} \times I_{cyclo}}{MU_{spot}} \text{ or}$$

$$c_{spot} = \frac{I_{cyclo}}{t_{spot} \times MU_{spot}} \text{ or}$$

$$c_{spot} = \frac{1 + I_{cyclo\,max} - I_{cyclo}}{MU_{spot} * t_{spot}} \text{ or, more generally,}$$

$$c_{spot} = f(t_{spot}, MU_{spot}, I_{cyclo}, I_{cyclo\,max}, p^*).$$

In the equations above, $c_{spot}$ represents the cost for an individual spot, $I_{cyclo}$ max represents the maximum possible cyclotron beam current, $I_{cyclo}$ represents the cyclotron beam current during the delivery of a spot, $MU_{spot}$ represents the MUs for an individual spot, $t_{spot}$ represents the time required to deliver an individual spot, and $p^*$ represents any other spot or beam production, energy selection, beam transport and/or beam delivery system parameter.

The total value of the cost function representing the total cost of the treatment plan can be determined according to a sum of the individual cost of all spots, where n is the total number of spots present in the plan:

$$\Sigma_{i=1}^{n} c_{spot_i}.$$

To optimize the treatment plan, the relatively costly spot or spots can be modified without significantly impacting dosimetry and treatment time. Generally speaking, modifying a spot may mean that the spot is removed from the treatment plan, or that the MLTs or dose contribution from the spot are distributed to one or more neighboring spots including spots in the same layer or spots in one or more adjacent layers, and/or that the locations (distribution) of the spots around the modified or removed spot can be adjusted (refer also to the discussion of FIG. 7 below).

According to some embodiments, the spots (for instance, spot weight) are automatically adjusted by the TPS to reduce the cost of the spot and the total cost of the treatment plan, thereby reducing the overall treatment time for delivering the treatment plan. The reduction of treatment time is significant for improving the quality of the treatment as well as patient comfort. Reducing treatment time for delivering a radiotherapy treatment plan can lower the risk of intra-fraction misalignment, increase machine throughput, and enable or facilitate specialized treatments, such as breath-hold immobilization treatments, thereby improving the quality of care and/or accessibility to the proton therapy. Embodiments according to the invention also allow such effective radiotherapy treatment plans to be generated quickly. Thus, embodiments according to the invention improve the field of radiation treatment planning specifically and the field of radiation therapy in general.

Figure 2:
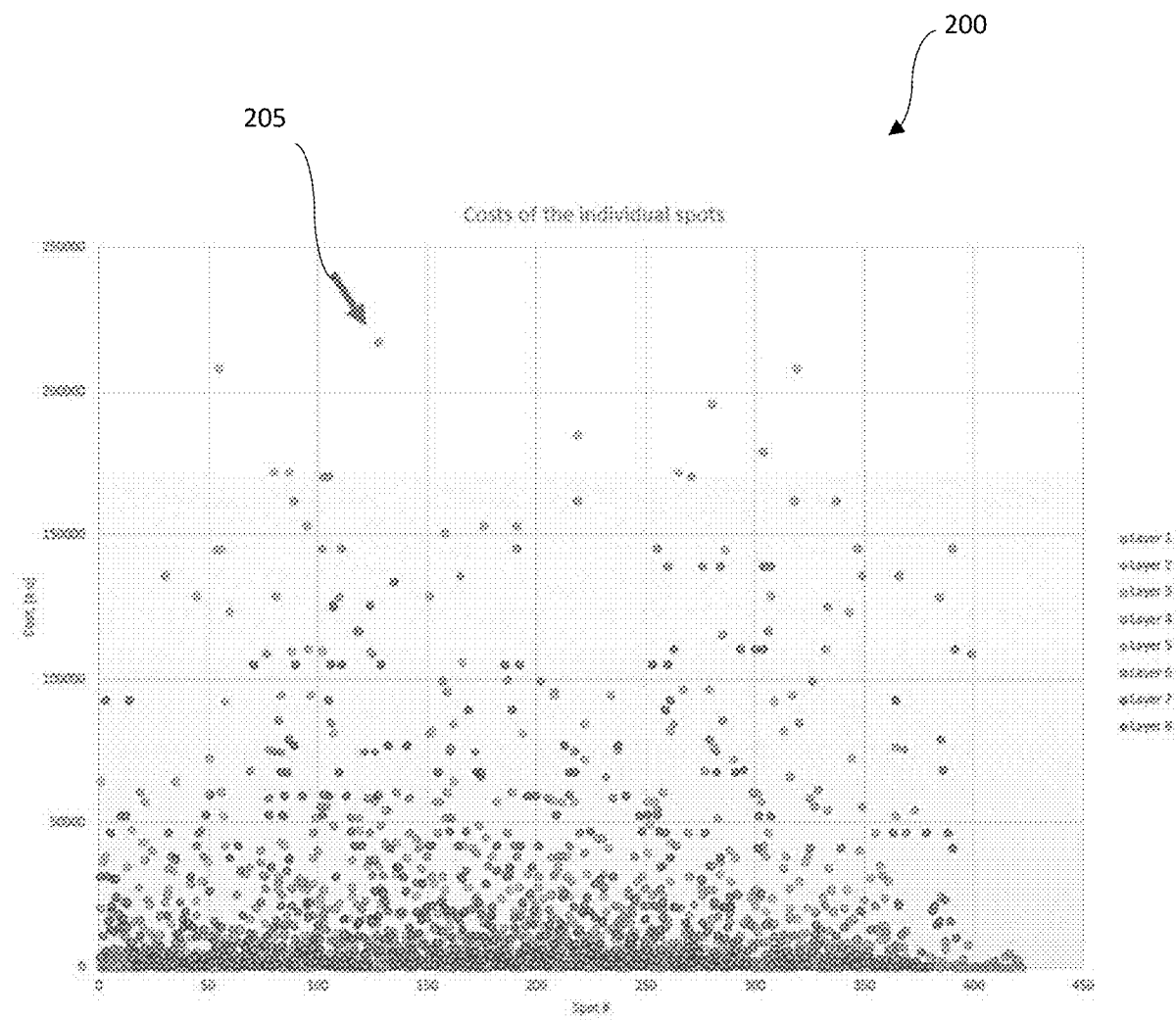
FIG. 2 is a graph depicting the cost per spot for the layers of an example of a treatment plan according to embodiments of the present invention.

In the example of FIG. 1, the total cost of the example treatment plan is 41,653,704.38 arbitrary units (AU). FIG. 2 is a graph 200 depicting the cost per spot for the layers (energy layers, also referred to herein as treatment layers or simply as layers) of the example treatment plan of FIG. 1 according to embodiments of the present invention.

In the example of FIG. 2, spots that are depicted higher in the graph 200 are associated with a higher time-wise cost than spots that are depicted lower in the graph 200. Spot 205 at the top of the graph 200 indicates the spot associated with the highest cost as determined by a cost function such as the cost function described above. By removing the spot 205 from a treatment (energy) layer, the total cost of the treatment plan with the modified layer can be reduced without significantly impacting dosimetry. After the elimination of the spot, the value of the cost function for the treatment plan with the modified layer can be recalculated according to machine-specific knowledge (e.g., timing constraints of the delivery system). Specifically, for the examples depicted in FIGS. 1-2, elimination of the spot 205 having the highest cost results in a reduction of the total cost of the treatment plan by 13,721.95 AU, and the field delivery time is reduced by 0.954 seconds, resulting in a field delivery time of 65.727 seconds compared to the original field delivery time of 66.681 seconds.

Figure 3:
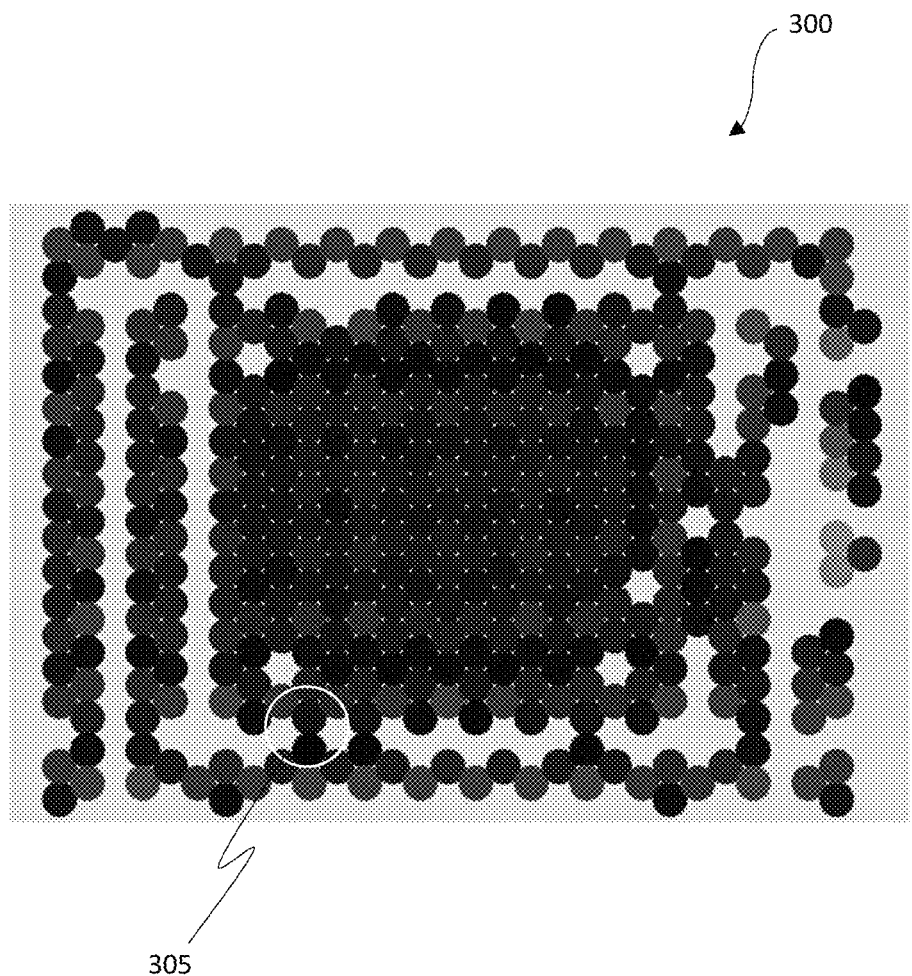
FIG. 3 depicts an example of a spot scanning pattern of a conventional treatment plan generated by a treatment planning system without time optimization or cost reduction.
Figure 4:
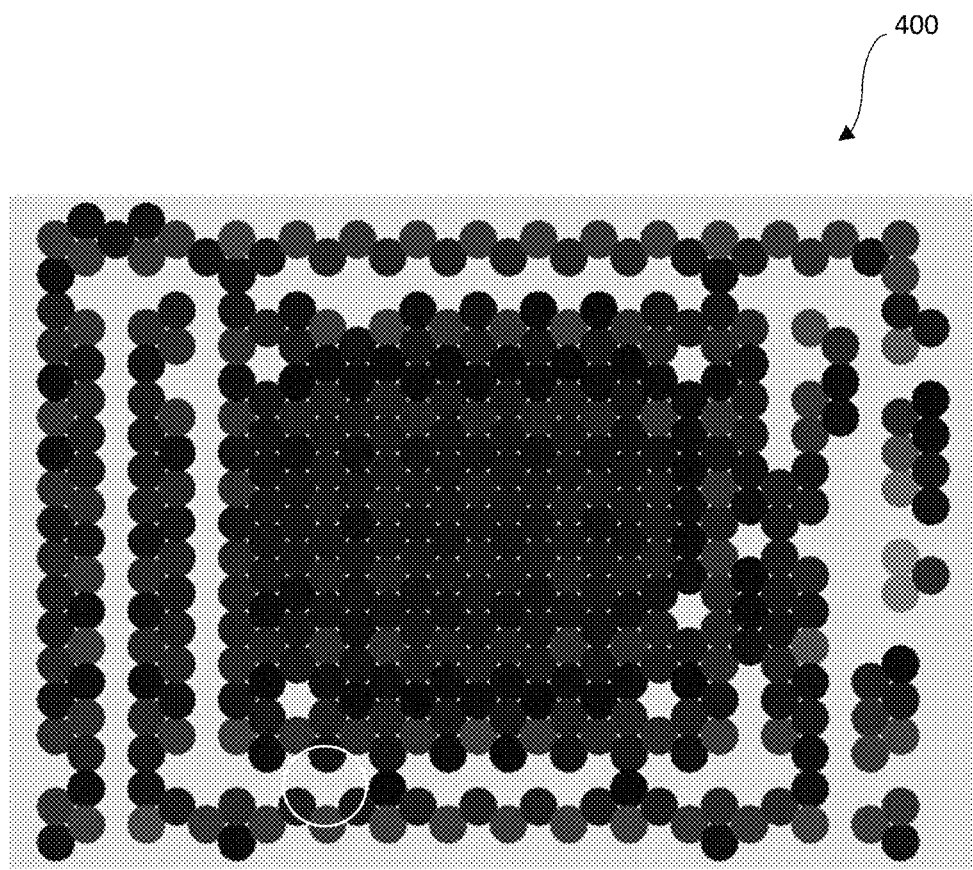
FIG. 4 depicts an example of a spot scanning pattern of a modified treatment plan having the time-wise highest cost spot removed according to embodiments of the present invention.
Figure 5:
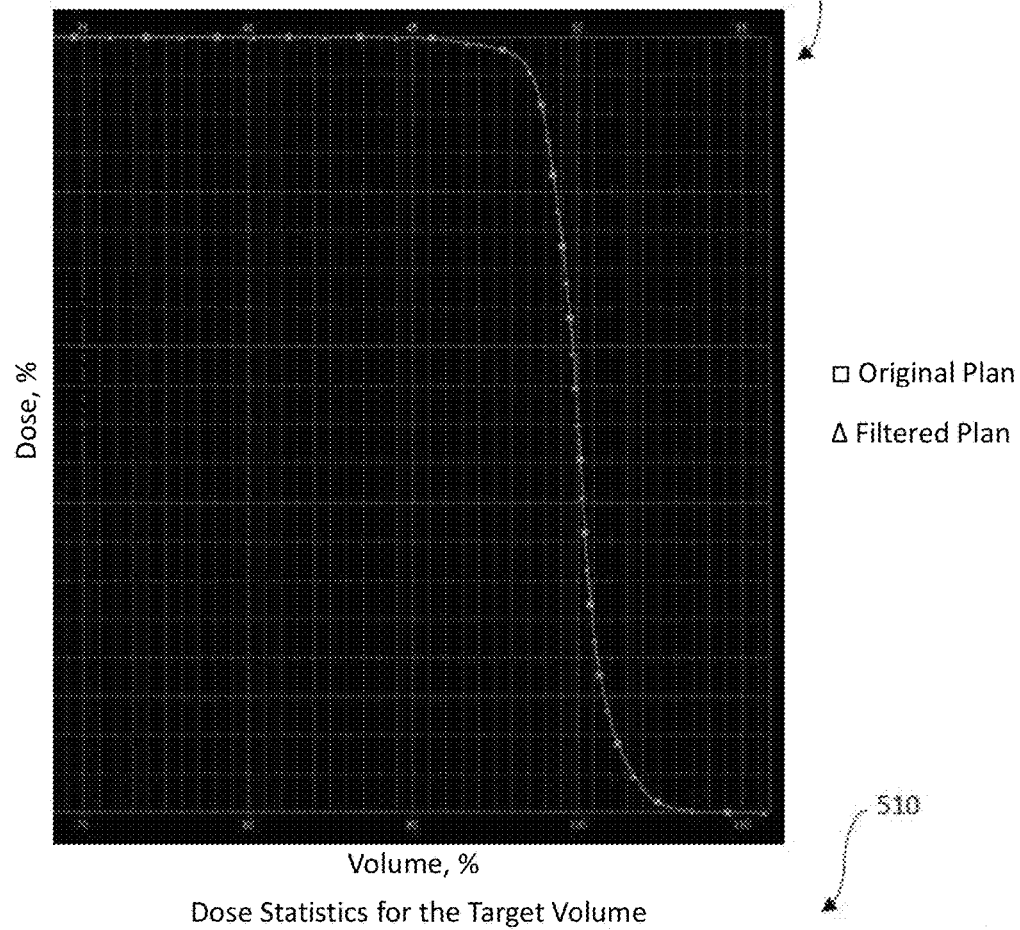
FIG. 5 depicts the dosimetry of the modified treatment plan of FIG. 4 compared to a conventional treatment plan without cost reduction.
Figure 5:

FIG. 3 depicts an example of a spot scanning pattern 300 of a conventional treatment plan generated by a TPS without optimization or cost reduction. In the example of FIG. 3, the spot 305 is the highest-cost spot, but none of the spots are removed from the original treatment plan on the basis of their time-wise cost. In comparison, FIG. 4 depicts an example of a spot scanning pattern 400 of a modified treatment plan having the highest-cost spot removed (the spot 305) according to embodiments of the present invention. The elimination of spot 305, as shown in FIGS. 3-4, has no significant dosimetric consequences on the plan quality and no impact on the dose statistics for the target, as shown in FIG. 5, which is discussed below. Thus, the total irradiation time during treatment can be reduced by not including the spot 305 in the treatment plan.

FIG. 5 is a dose-volume histogram (DVH) depicting the dosimetry of a treatment plan modified according to embodiments of the present invention compared to a conventional treatment plan that is not modified. As depicted in FIG. 5, the dosimetry and treatment quality 505 of the modified treatment plan with the reduced total cost are not significantly affected, and no impact on the dose statistics for the target structure is observed in the table 510; however, treatment time is advantageously reduced.

Figure 6:
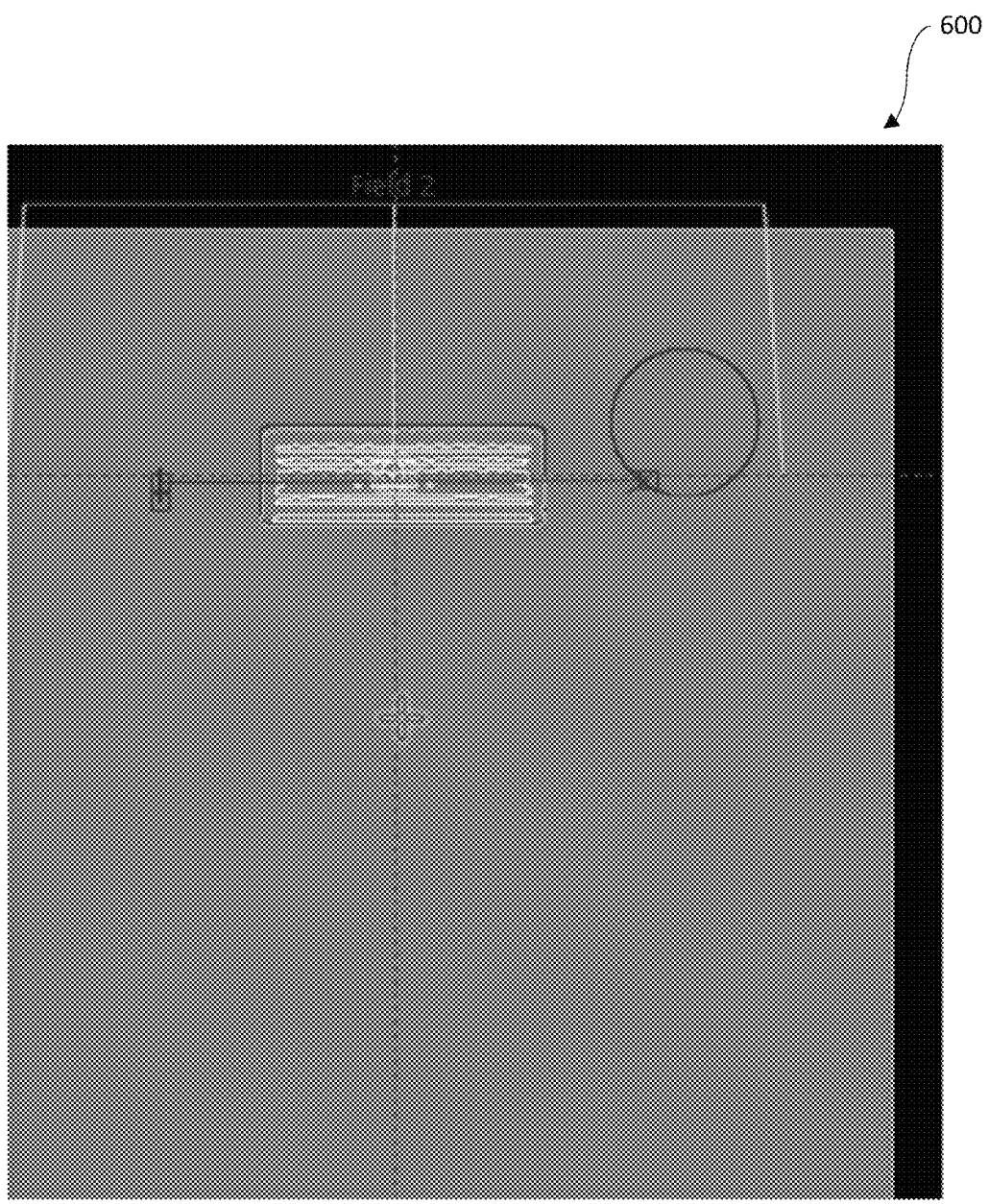
FIG. 6 depicts isodose lines of an example of an optimized radiotherapy treatment plan with significant time-wise cost reduction according to embodiments of the present invention.

FIG. 6 depicts isodose lines 600 of an example of a radiotherapy treatment plan generated and optimized according to embodiments of the present invention. The treatment plan is generated by a radiotherapy TPS and is used to control a radiotherapy system (e.g., a proton therapy treatment system) for delivering a prescribed dose of radiation. In the example of FIG. 6, relative to the example of FIG. 1, for example, the treatment plan is reduced substantially to a total cost function value of 14,912.01 AU using eight energy layers and 1872 total spots. Moreover, the delivery time of the treatment plan is advantageously and significantly reduced to 25.285 seconds compared to the original treatment time of 66.681 seconds (Table I). The treatment time for the different layers determined based on machine-specific parameters is represented below in Table II.

TABLE II

| Layer Number | Energy [MEV] | Number Of Spots | Total Irradiation Time [sec] |
| --- | --- | --- | --- |
| 1 | 131.62 | 234 | 25.285 |
| 2 | 128.12 | 234 | |
| 3 | 124.62 | 234 | |
| 4 | 121.12 | 234 | |
| 5 | 117.62 | 234 | |
| 6 | 114.12 | 234 | |
| 7 | 110.62 | 234 | |
| 8 | 107.12 | 234 | |

Figure 7:
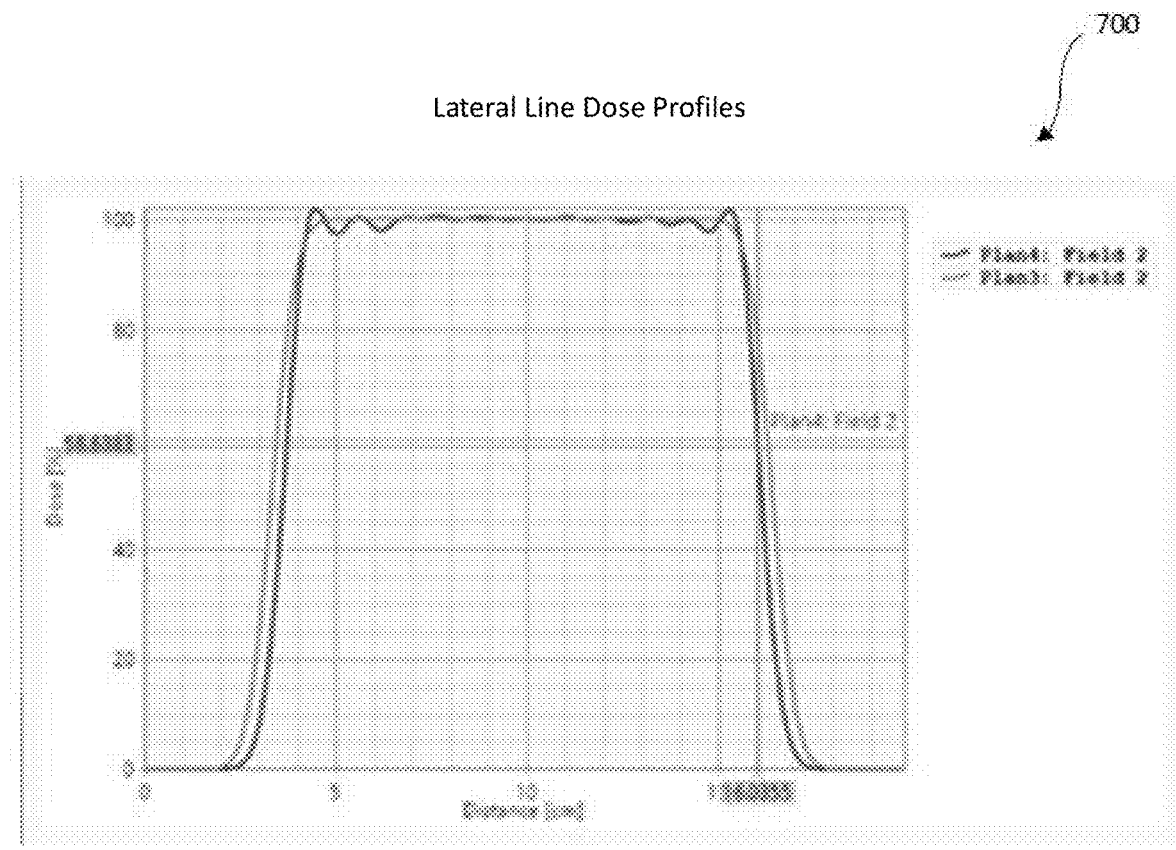
FIG. 7 illustrates lateral line dose profiles for two example radiotherapy treatment plans, according to embodiments of the present invention.

While target volume dose statistics are maintained and comparable to the original plan, reduction in dose conformality may result in increased dose to the organs at risk (OARs), which can be observed in graph 700 of FIG. 7, which shows lateral line dose profiles for two example radiotherapy treatment plans. More specifically, in the example of FIG. 7, plan 3 (which, relative to plan 4, is a faster plan with respect to delivery time) has a broader lateral penumbra that may result in higher OAR doses relative to plan 4, while plan 4 (which, relative to plan 3, is a slower plan with respect to delivery time) has a sharper lateral penumbra, which may result in lower OAR doses relative to plan 3. Therefore, according to some embodiments, rather than removing a spot and its associated dose contribution, the dose contribution of that spot can be redistributed to neighboring spots, which can advantageously reduce the overall dosimetric impact of treatment time optimization/reduction in certain cases.

Figure 8:
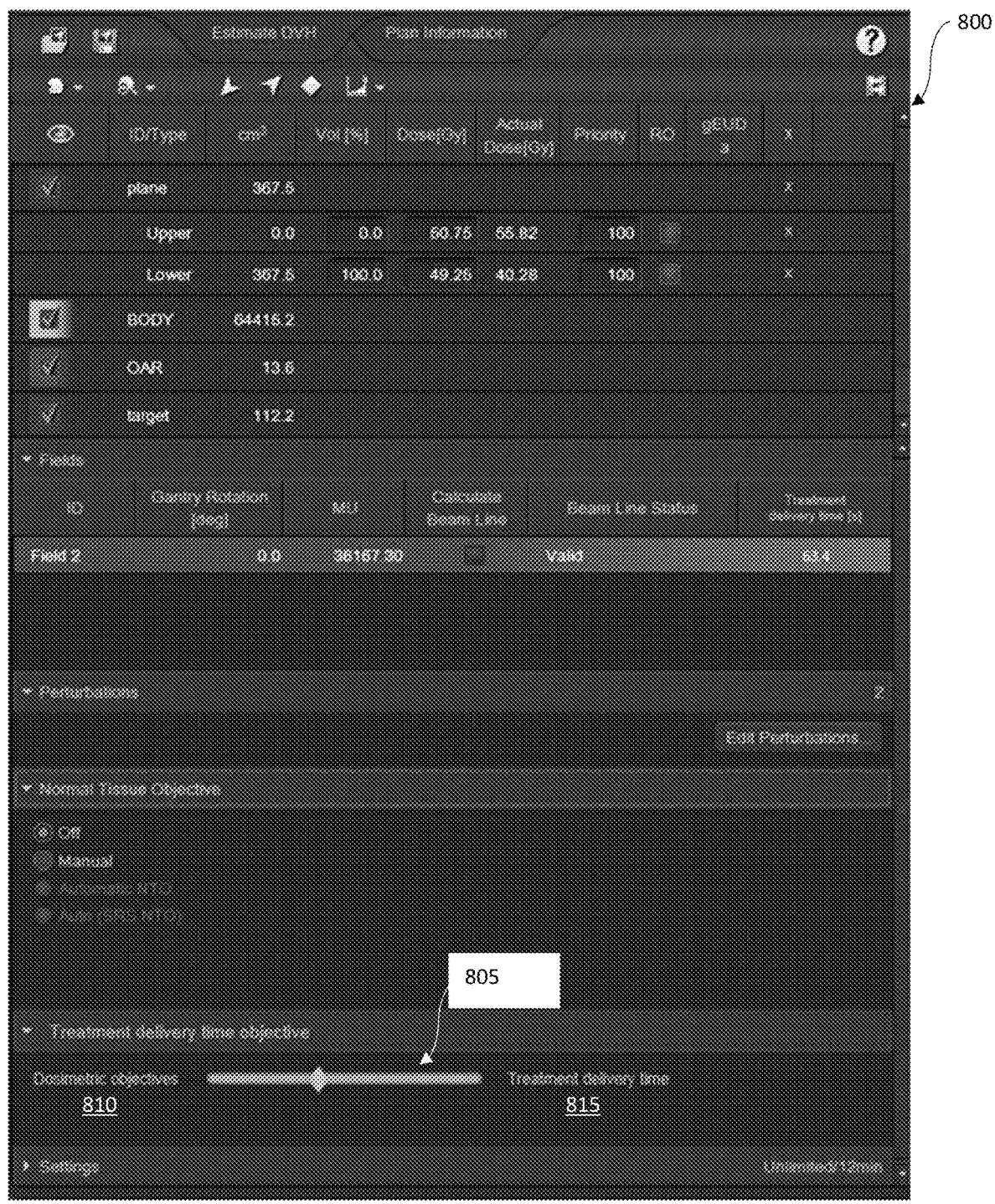
FIG. 8 is an on-screen display of an example of a graphical user interface of a treatment planning system including a controller (e.g., a slider) for assigning relative weights to dosimetric objectives and treatment time objectives used to generate an optimized treatment plan with a reduced total cost by removing one or more spots, according to embodiments of the present invention.
Figure 10:
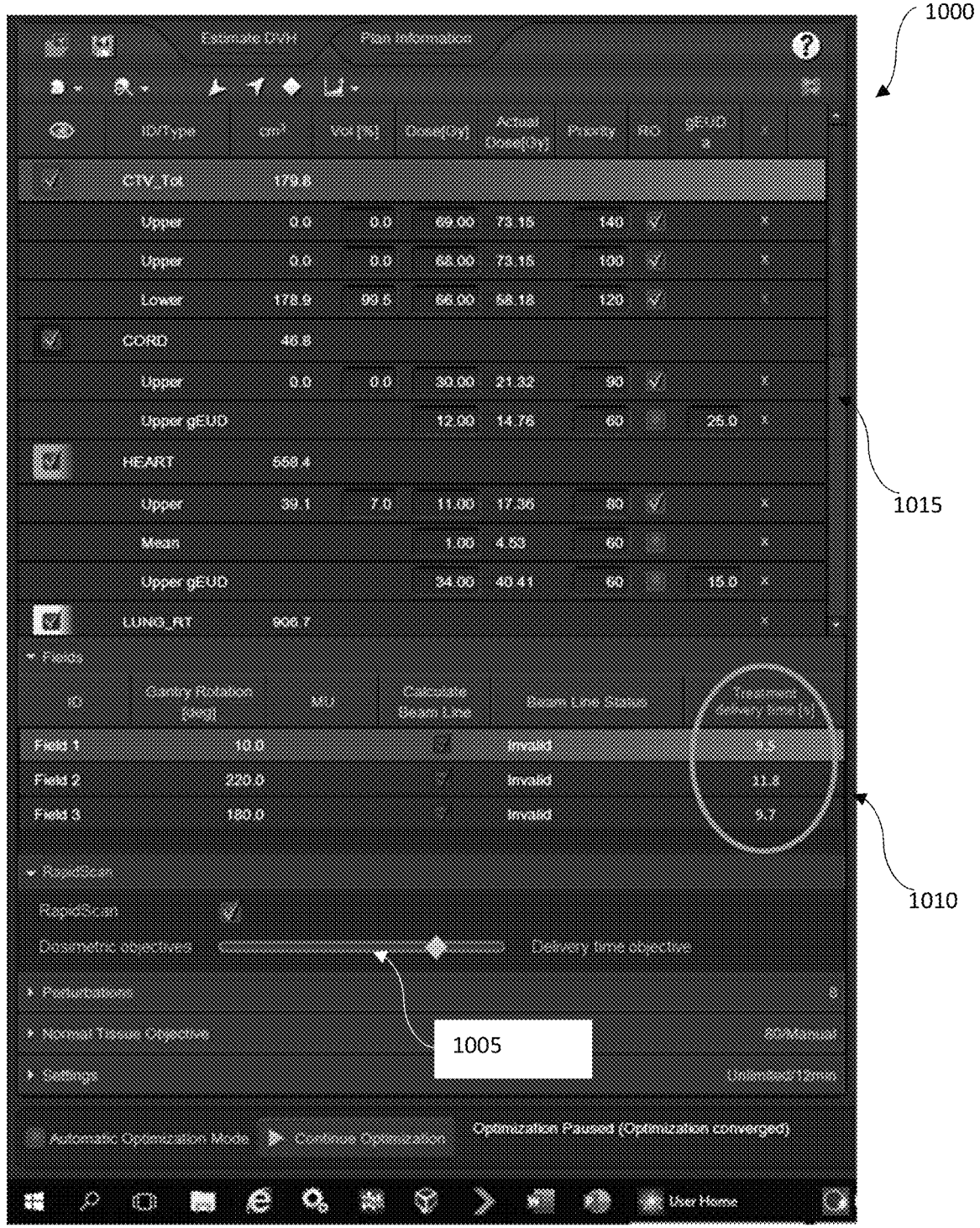
FIG. 10 is an on-screen display of an example of a graphical user interface of a treatment planning system including a list of treatment delivery times for fields of a treatment plan generated using spot reduction to reduce the treatment delivery time according to delivery time objectives (e.g., timing constraints of the delivery system) while also considering dosimetric objectives of the treatment plan, according to embodiments of the present invention.
Figure 11A:
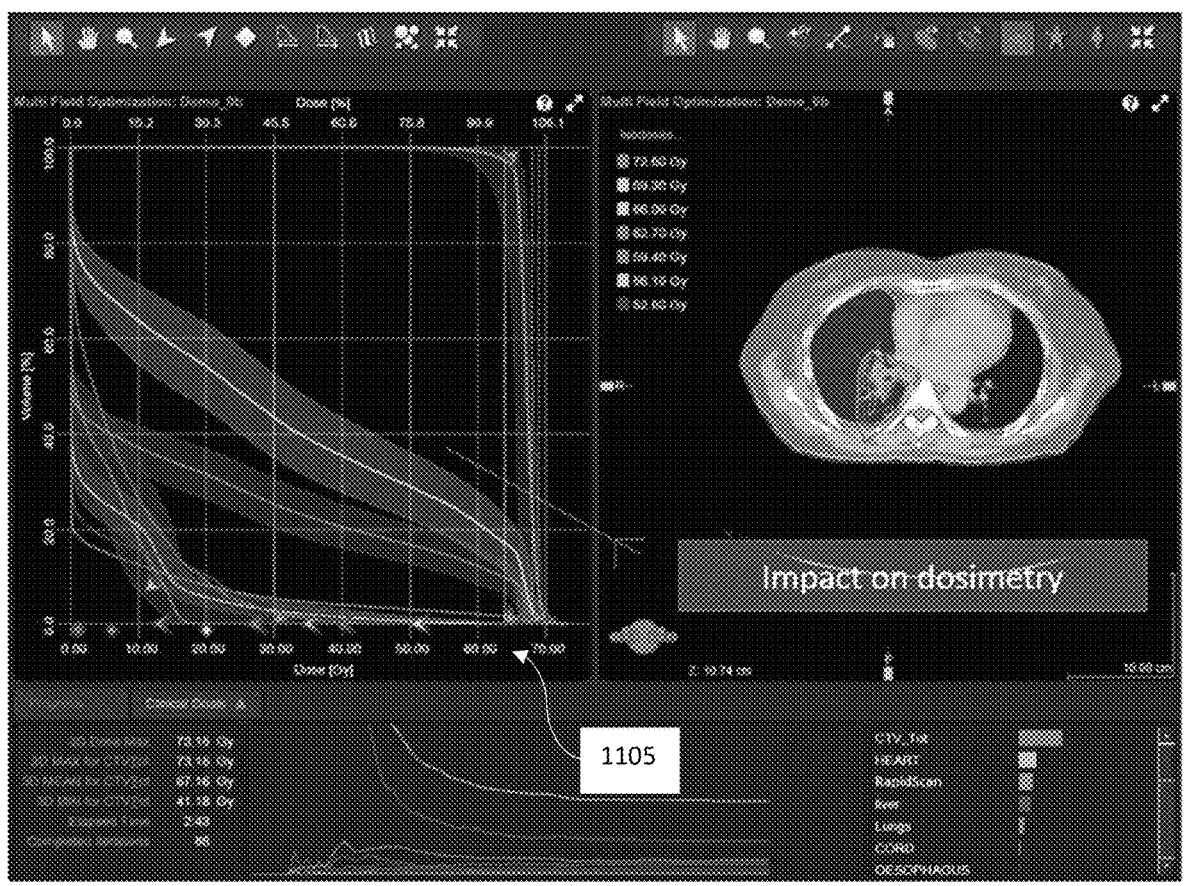
FIGS. 11A and 11B are on-screen displays of an example of a graphical user interface of a treatment planning system including a dose-volume histogram and a scanning pattern and sequence generated dynamically in accordance with relative weights assigned to treatment time objectives and dosimetric objectives of the treatment plan, according to embodiments of the present invention.

As mentioned above, machine-specific knowledge can be used by a treatment planning system to generate a cost function for optimizing the field delivery time, for example, according to timing constraints of the delivery system. Some embodiments of the present invention can generate an optimized treatment plan based on a prescribed balance between field delivery time and dosimetric characteristics according to user input received by the TPS, e.g., via a graphical user interface (GUI). For example, as depicted in FIG. 8, the end 815 of the slider 805 displayed on graphical the GUI 800 biases the optimization of the treatment plan toward reducing delivery time, and the end 810 of the slider 805 biases the optimization of the treatment plan toward minimizing dosimetric impact and/or satisfying dosimetric objectives. The value in the middle of the slider prioritizes reduced treatment time and dosimetric impact equally to achieve a balance between treatment time and treatment quality/dosimetry. Adjusting the slider by interacting with the GUI 800 dynamically updates the delivery time information and the respective dose distributions and dose-volume histogram (DVH) curves, as depicted in FIGS. 10 and 11A, by performing plan optimization to remove the costliest spot or spots. Of course, other forms of input can be used to define the respective weights of treatment time reduction and preservation of dosimetry, such as buttons, numeric input fields, etc.

Figure 9:
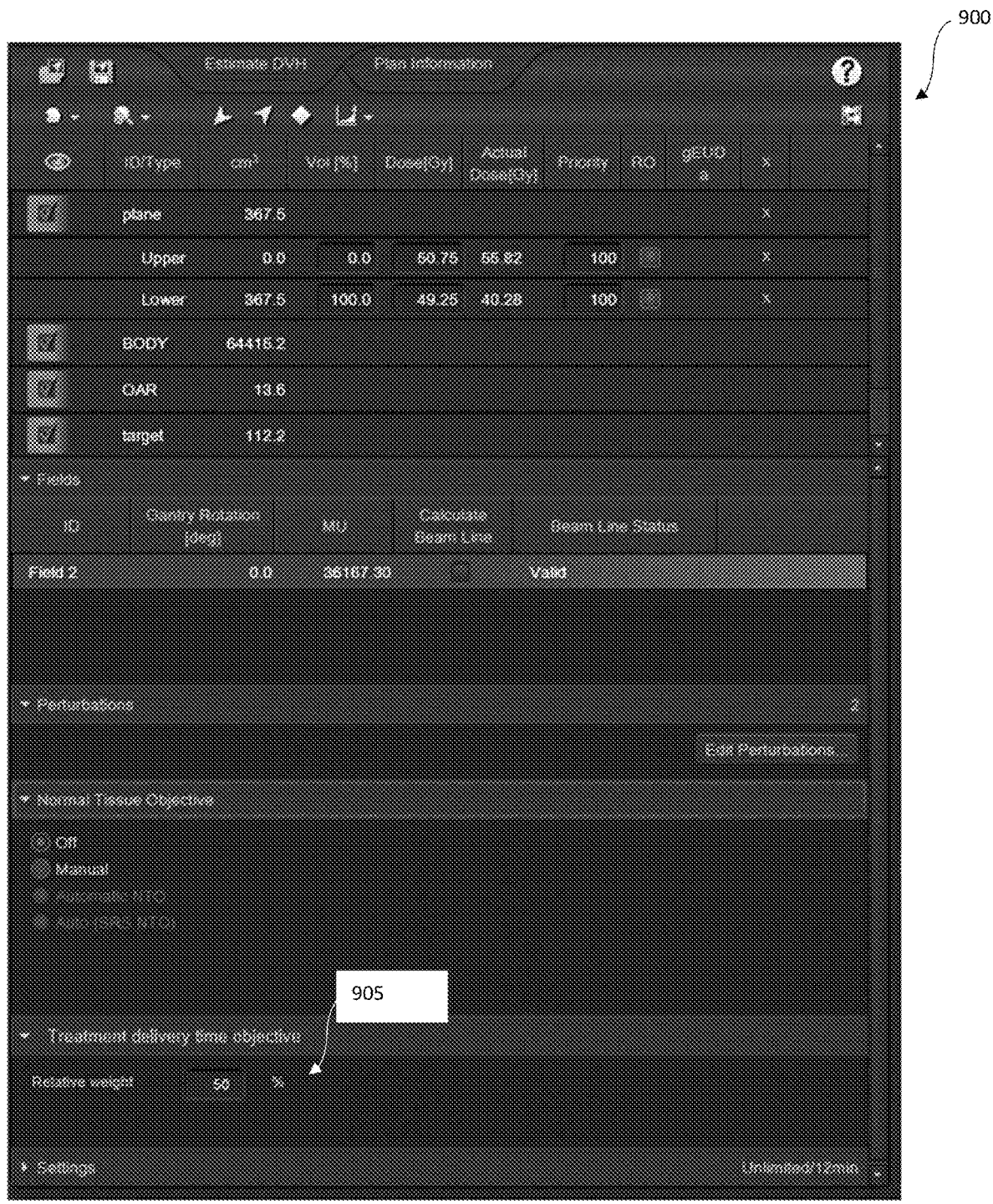
FIG. 9 is an on-screen display of an example of a graphical user interface of a treatment planning system including an input field for assigning a relative weight to treatment time objective versus dosimetric objectives used to generate an optimized treatment plan with a reduced total cost by removing one or more spots, according to embodiments of the present invention.

In the example of FIG. 9, the example on-screen graphical user interface 900 includes a numeric input field 905 for defining the relative weight of a treatment time objective (e.g., the treatment delivery time objective). A value between zero and 100 can be entered by the end user to assign zero weight to the treatment delivery time when optimizing the treatment plan, full weight (100) such that dosimetric objectives are not considered at all, or a weight between zero and 100 that optimizes the resultant treatment plan based on a weighted combination of treatment time reduction and dosimetric objectives. Other optimization objectives linked to dosimetric characteristics of the plan, such as DVH objectives, equivalent uniform dose (EUD) objectives, minimum and maximum dose objectives, dose fall-off (or normal tissue) objectives, etc., can be considered during optimization. Moreover, these objectives can be defined as being robust for multi-scenario optimization. In an embodiment, the complete set of these objectives can be considered as "dosimetric objectives" for optimization purposes.

FIG. 10 depicts an example of an on-screen graphical user interface 1000 including a slider 1005 that defines the respective weights of the dosimetric objectives and delivery time objectives for generating an optimized treatment plan, for example, to reduce the delivery time without significant dosimetric impact according to embodiments of the present invention. Adjusting the slider 1005 in the GUI 1000 dynamically updates the delivery time information 1010 and the respective dose distributions 1015. In this way, a user can conveniently and efficiently define different weights for dosimetric objectives and delivery time objectives, and immediately view the resultant impact on treatment delivery time and dose distribution. When the desired balance is achieved, an optimized treatment plan can be generated for delivering the prescribed radiotherapy treatment as defined by the optimized treatment plan, advantageously resulting in better overall treatment quality and/or reduced treatment time.

Figure 11B:
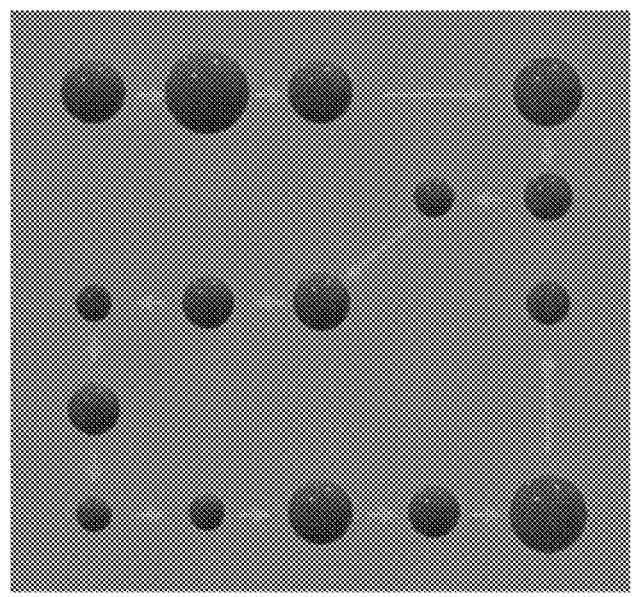

FIGS. 11A and 11B depict an example of an on-screen graphical user interface 1100 including a DVH 1105 and a spot scanning pattern 1110 produced in response to values defined by the slider 1005 in FIG. 10 according to embodiments of the present invention. Any common form of data entry can be used to define the respective weights of the dosimetric objectives and delivery time objectives for generating an optimized treatment plan. By observing the DVH 1105 and the spot scanning pattern 1110 corresponding to different weights of dosimetric and delivery time objectives, an optimized plan can be generated that satisfies the specific needs of the radiotherapy treatment as determined by the user input of a clinician, for example, considering any specific constraints of the delivery system.

The actual dose delivered by a treatment delivery machine often differs from the static dose defined by a radiotherapy treatment plan. Accordingly, some embodiments of the present invention can be used as a validation measure to ensure that the dose actually delivered to the patient is reasonable and conforms with quality control measures implemented for patient safety. For example, delivery dynamics at the treatment machine can significantly impact the dose actually delivered by the treatment delivery machine compared to the planned static dose distribution in the treatment planning system. Therefore, the treatment planning system can be equipped with a model of the machine-specific delivery dynamics and/or parametrizations to perform a simulated delivery of the treatment plan and provide resultant metrics to evaluate the delivered dose distribution compared to the planned dose distributions of the radiotherapy treatment plan. In this way, unsafe or impractical treatments can be identified and avoided as a safety/quality control measure, and a more optimal treatment plan can be generated that delivers a safe and high-quality dose distribution to effectively treat a target volume in conformity with a health or safety quality standard, for example.

While several embodiments of the present invention disclosed herein generate optimized treatment plans for proton therapy, embodiments of the present invention are also well-suited to other forms of radiotherapy treatment (such as electron beams, photon beams, ion beams, or atom nuclei beams (e.g., carbon, helium, and lithium)). Moreover, the spot filtering optimization processes disclosed herein for reducing the total cost of a treatment plan can be used for dose rate optimization in biology-driven treatment planning and FLASH applications where timing is linked to potential response mechanisms, including but not limited to preventing radiation induced hypoxia and DNA damage/repair. The spot filtering optimization process of the embodiments of the present invention can also be used to filter and redistribute dose across fields to take advantage of full intensity modulation capabilities of the treatment delivery machine. For example, a spot that contributes significantly to both delivery time and dose may be cross-examined amongst other contributing fields to determine if another layer from a different field contributes to the dose in a more time-efficient manner.

According to some embodiments, penalization and further extensions of the cost function are also considered. For example, additional penalties can be associated with fields that require tighter time restrictions due to treatments and beam orientations that may be affected by patient motion. When a plan requires a four-dimensional computed tomography (4DCT) scan during the patient simulation, deformable image registration can be performed between end-of-inhale and end-of-exhale phases. Based on the obtained deformation vector fields, it is possible to determine the predominant motion direction and penalize dose contribution from the spots (fields) directed perpendicular to the primary motion direction, while favoring spots (fields) directed more parallel to the primary motion direction, thereby tailoring the plan to patient-specific needs.

Figure 12:
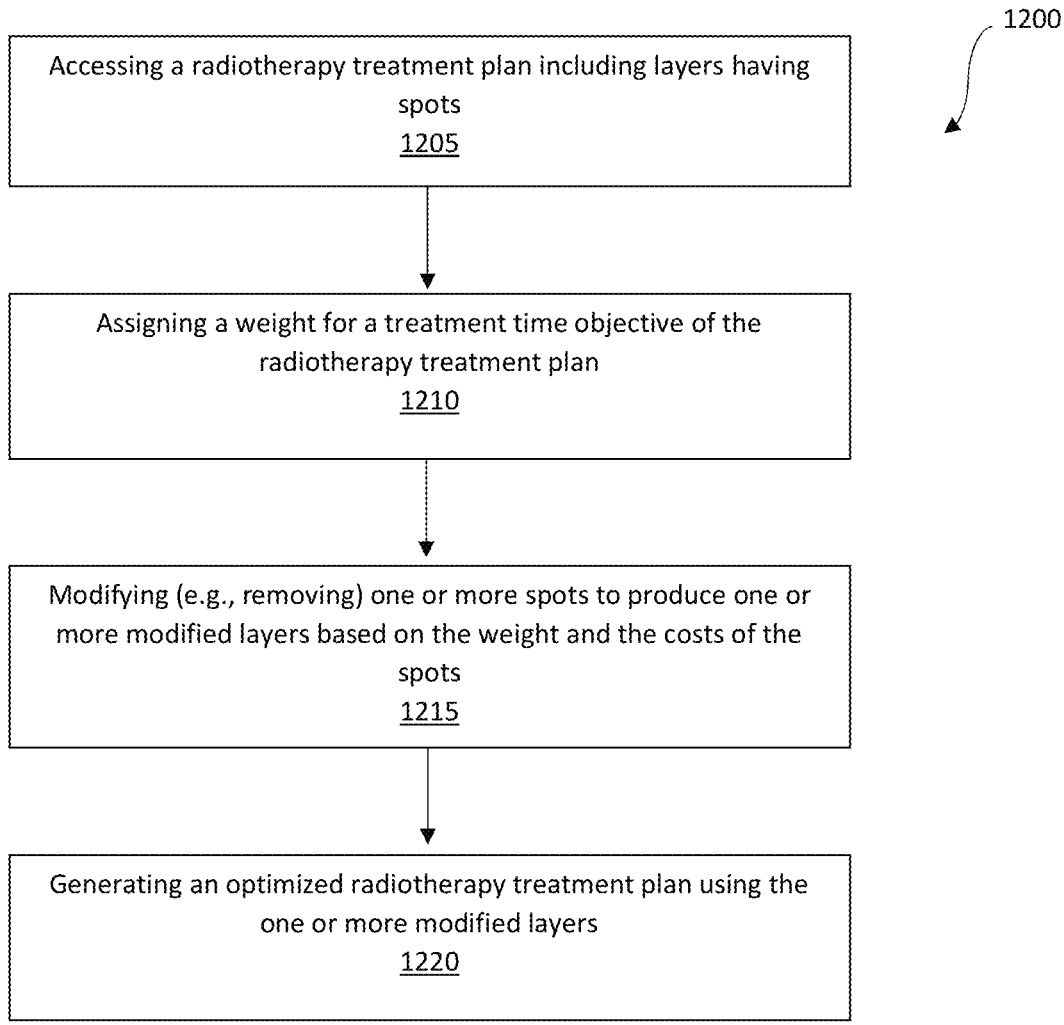
FIG. 12 is a flowchart of an example of a sequence of computer-implemented steps in a method for optimizing a radiotherapy treatment plant to reduce the total cost/delivery time, according to embodiments of the present invention.

FIG. 12 is a flowchart depicting an example of a sequence of computer-implemented steps of a method or process 1200 for producing an optimized radiotherapy treatment plan that achieves a desired balance between field delivery time and dose based on machine parameters and knowledge, such as machine-specific scanning logic, and/or a maximum treatment time value. The process 1200 may be implemented as program code (instructions) stored in a non-transitory computer-readable storage medium (memory) and executed on a processor.

At a step 1205, a radiotherapy treatment plan is accessed by or generated by a radiotherapy treatment planning system. The radiotherapy treatment plan includes a plurality of (one or more) treatment players having spots with associated doses. The treatment delivery time of the spots can be determined according to machine-specific knowledge associated with a delivery machine for delivering radiotherapy treatment in accordance with the treatment plan. The cost of a spot can be determined according to the dose and the treatment delivery time.

At a step 1210, a weight is assigned to a treatment time objective of the radiotherapy treatment plan. The treatment time objective can include reducing the overall treatment time or setting a maximum treatment time, for example.

At a step 1215, one or more spots of the layers of the radiotherapy treatment plan are modified (e.g., removed or redistributed as described above) based on the cost of a respective spot and the weight assigned to the treatment time objective. According to some embodiments, the one or more spots are modified according to a weight assigned to a dosimetric objective of the treatment planning system. The dosimetric objectives can include, for instance, DVH objectives, equivalent uniform dose (EUD) objectives, minimum and maximum dose objectives, dose fall-off (or normal tissue) objectives, and the like. According to some embodiments, the spots are automatically adjusted by the TPS to reduce the cost of the spot and the total cost of the treatment plan, thereby reducing the overall treatment time for delivering the treatment plan. According to some embodiments, MUs from spots of a layer can be redistributed to spots of an adjacent layer, or a layer can be removed and the spots of that layer can be redistributed.

At a step 1220, an optimized radiotherapy treatment plan is generated according to the layers modified in the step 1215 and saved to computer memory.

Embodiments of the present invention are drawn to computer systems for planning and optimizing a radiotherapy treatment plan to reduce the delivery time of radiotherapy treatment according to machine-specific knowledge as described above. A user can enter a value, e.g., using a GUI, that defines the relative weight applied to delivery time objectives compared to dosimetric objectives by removing relatively costly spots without significant dosimetric impact. As noted above, because of the different parameters that need to be considered, the range of values for those parameters, the interrelationship of those parameters, the need for treatment plans to be effective yet minimize risk to the patient, and the need to generate high-quality treatment plans quickly, the use of a treatment planning system executing consistently on a computer system for radiation treatment planning as disclosed herein is important. The following discussion describes an example of such a computer system.

Figure 13:
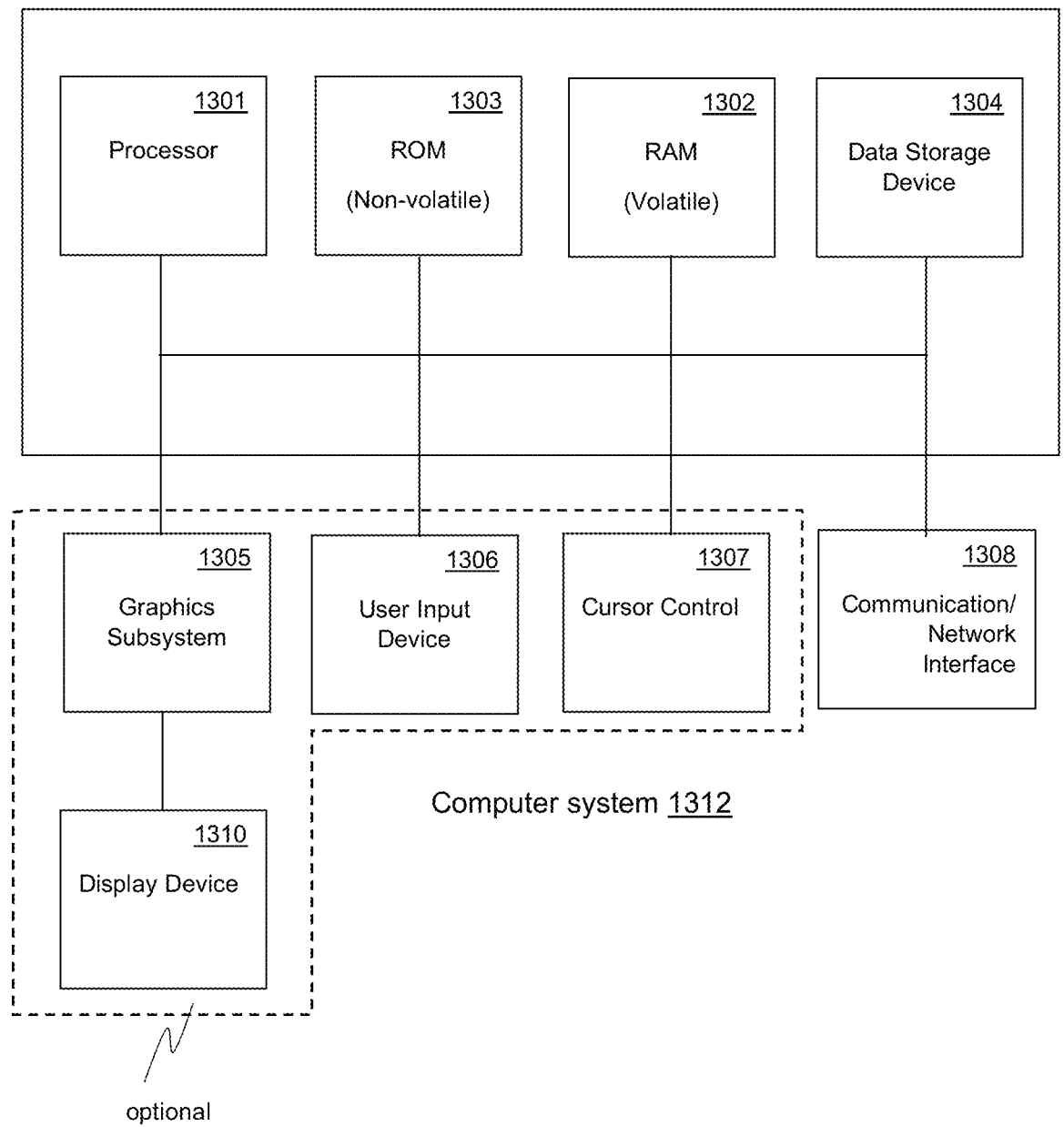
FIG. 13 is a block diagram depicting an example of an electronic system upon which embodiments of the present invention can be implemented.

In the example of FIG. 13, the electronic or computer system 1312 includes a central processing unit (CPU) 1301 for running software applications (e.g., a radiotherapy treatment planning system) and optionally an operating system. Computer memory includes random access memory 1302 and/or read-only memory 1303, which store applications and data for use by the CPU 1301. A data storage device 1304 provides non-volatile storage for applications and data and may include fixed disk drives, removable disk drives, flash memory devices, and CD-ROM, DVD-ROM or other optical storage devices. The optional user inputs 1306 and 1307 comprise devices that communicate inputs from one or more users to the computer system 1312 (e.g., mice, joysticks, cameras, touch screens, and/or microphones).

The computer system memory includes computer-readable instructions, data structures, program modules, and the like associated with a treatment planning system. The treatment planning system may be distributed over some combination of the computer storage media, or may be distributed over some combination of networked computers. The treatment planning system is used to evaluate and produce a radiotherapy treatment plan in accordance with the embodiments disclosed herein.

A communication or network interface 1308 allows the computer system 1312 to communicate with other computer systems, networks, or devices via an electronic communications network, including wired and/or wireless communication and including an Intranet or the Internet. The display device 1310 may be any device capable of displaying visual information in response to a signal from the computer system 1312 and may include a flat panel touch sensitive display, for example. The components of the computer system 1312, including the CPU 1301, memories 1302 and 1303, data storage 1304, user input devices 1306, and graphics subsystem 1305 may be coupled via one or more data buses.

In the embodiment of FIG. 13, the graphics subsystem 1305 is optional and may be coupled with the data bus and the components of the computer system 1312. The graphics system 1305 may comprise a physical graphics processing unit (GPU) and graphics/video memory. The GPU may include one or more rasterizers, transformation engines, and geometry engines, and generates pixel data from rendering commands to create output images. The physical GPU can be configured as multiple virtual GPUs that may be used in parallel (e.g., concurrently) by a number of applications or processes executing in parallel, or multiple physical GPUs may be used simultaneously. The graphics subsystem 1305 can output display data to the display device 1310, for example, to visualize DVHs and dose distributions of modified treatment plans, and to render sliders or input fields on the display device 1310 with graphical user interfaces.

In radiation therapy techniques in which the intensity of the particle beam is either constant or modulated across the field of delivery, such as in intensity modulated radiation therapy (IMRT), intensity modulated particle therapy (IMPT), and spot scanning (e.g., pencil beam scanning), beam intensity is varied across each treatment region (volume in a treatment target) in a patient. Depending on the treatment modality, the degrees of freedom available for intensity modulation include, but are not limited to, beam shaping (collimation), beam weighting (spot scanning), number and arrangement of spots, and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments of the present invention are thus described. While the present invention has been described in particular embodiments, the present invention should not be construed as limited by such embodiments, but rather construed according to the following claims.

What is claimed is:

1. A computer-implemented method for radiotherapy treatment planning, the computer-implemented method comprising:
   accessing a radiotherapy treatment plan including a plurality of treatment layers, each treatment layer of the plurality of treatment layers including a plurality of spots;
   receiving a weight for a treatment time objective of the radiotherapy treatment plan;
   modifying a spot from a treatment layer of the plurality of treatment layers based on the weight and a cost of the spot, to produce a modified treatment layer; and
   generating a modified radiotherapy treatment plan using the modified treatment layer, wherein the modified radiotherapy treatment plan is operable to be executed by a delivery machine to apply radiotherapy treatment to a target in accordance with the modified radiotherapy treatment plan.

2. The computer-implemented method as described in claim 1, further comprising:
   modifying a plurality of spots of the plurality of treatment layers to produce a plurality of modified treatment layers, wherein said generating the modified radiotherapy treatment plan is performed using the plurality of modified treatment layers.

3. The computer-implemented method as described in claim 1, wherein said modifying a spot comprises:
   removing the spot;
   modifying the spot to reduce the cost of the spot; or
   redistributing a dose contribution of the spot to one or more neighboring spots.

4. The computer-implemented method as described in claim 1, further comprising:
   receiving a weight for a dosimetric objective of the radiotherapy treatment plan.

5. The computer-implemented method as described in claim 4, wherein the dosimetric objective comprises:
   a dose-volume histogram (DVH) objective;
   an equivalent uniform dose (EUD) objective;
   a minimum dose objective;
   a maximum dose objective; or
   a dose fall-off objective.

6. The computer-implemented method as described in claim 4, further comprising:
   dynamically rendering a dose-volume histogram on a graphical user interface of a treatment planning system based on the weight for the treatment time objective of the modified radiotherapy treatment plan and the weight for the dosimetric objective of the radiotherapy treatment plan.

7. The computer-implemented method as described in claim 4, wherein the weight for the treatment time objective and the weight for the dosimetric objective are defined according to a position of a respective slider rendered on a graphical user interface of a treatment planning system.

8. The computer-implemented method as described in claim 1, further comprising:
   simulating a radiotherapy treatment according to the modified radiotherapy treatment plan to determine if an actual dose, when applied according to the modified radiotherapy treatment plan, will conform with a threshold quality standard for treatment.

9. The computer-implemented method as described in claim 1, wherein said modifying a spot comprises:

calculating a cost for each spot of the plurality of spots based on a dose associated with the spot and a delivery duration of the spot; and modifying at least one spot of the plurality of spots having a highest cost.

10. An electronic system for radiotherapy treatment planning, the electronic system comprising:

a display device;

a memory coupled to the display device; and a processor in communication with the memory, wherein the processor is configured to execute instructions to cause the electronic system to access a radiotherapy treatment plan including a plurality of treatment layers, each treatment layer of the plurality of treatment layers including a plurality of spots, assign a weight for a treatment time objective of the radiotherapy treatment plan using input received from a graphical user interface rendered on the display device, modify a spot from a treatment layer of the plurality of treatment layers based on the weight and a cost of the spot, to produce a modified treatment layer, and generate a modified radiotherapy treatment plan using the modified treatment layer, wherein the modified radiotherapy treatment plan is operable to be executed by a delivery machine to apply radiotherapy treatment to a target in accordance with the modified radiotherapy treatment plan.

11. The electronic system as described in claim 10, further comprising:

modifying a plurality of spots of the plurality of treatment layers to produce a plurality of modified treatment layers, wherein said generating the modified radiotherapy treatment plan is performed using the plurality of modified treatment layers.

12. The electronic system as described in claim 10, wherein modification of the spot includes:

removing the spot;

modifying the spot to reduce the cost of the spot; or redistributing a dose contribution of the spot to one or more neighboring spots.

13. The electronic system as described in claim 10, wherein the processor is configured to execute instructions to cause the electronic system to assign a weight for a dosimetric objective of the radiotherapy treatment plan.

14. The electronic system as described in claim 13, wherein the dosimetric objective includes:

a dose-volume histogram (DVH) objective;

an equivalent uniform dose (EUD) objective;

a minimum dose objective;

a maximum dose objective; or a dose fall-off objective.

15. The electronic system as described in claim 13, wherein the processor is configured to execute instructions to cause the electronic system to dynamically render a dose-volume histogram on the graphical user interface based on the weight for the treatment time objective of the modified radiotherapy treatment plan and the weight for the dosimetric objective of the modified radiotherapy treatment plan.

16. The electronic system as described in claim 13, wherein the weight for the treatment time objective and the weight for the dosimetric objective are defined according to a position of a respective slider rendered on the graphical user interface.

17. The electronic system as described in claim 10, wherein the processor is configured to execute instructions to cause the electronic system to simulate a radiotherapy treatment according to the modified radiotherapy treatment plan to determine if an actual dose, when applied according to the modified radiotherapy treatment plan, will conform with a threshold quality standard.

18. The electronic system as described in claim 10, wherein modification of the spot comprises:

calculating a cost for each spot of the plurality of spots based on a dose associated with the spot and a delivery duration of the spot; and modifying at least one spot of the plurality of spots having a highest cost.

19. A non-transitory computer-readable storage medium embodying instructions that, when executed by a processor, cause the processor to perform a method of radiotherapy treatment planning, the method comprising:

accessing a radiotherapy treatment plan including a plurality of treatment layers, each treatment layer of the plurality of treatment layers including a plurality of spots;

assigning a weight for a treatment time objective of the radiotherapy treatment plan based on received inputs;

modifying a spot from a treatment layer of the plurality of treatment layers based on the weight and a cost of the spot to produce a modified treatment layer; and generating a modified radiotherapy treatment plan using the modified treatment layer, wherein the modified radiotherapy treatment plan is operable to be executed by a delivery machine to apply radiotherapy treatment to a target in accordance with the modified radiotherapy treatment plan.

20. The non-transitory computer-readable storage medium as described in claim 19, wherein the method further comprises:

modifying a plurality of spots from the plurality of treatment layers to produce a plurality of modified treatment layers, wherein said generating a modified radiotherapy treatment plan is performed using the plurality of modified treatment layers.

* * * * *